United States Patent [19]

Matthew et al.

[11] Patent Number: 5,672,685
[45] Date of Patent: Sep. 30, 1997

[54] SOURCE OF APOLIPOPROTEIN E AND METHOD OF ISOLATING APOLIPOPROTEIN E

[75] Inventors: William D. Matthew; Warren J. Strittmatter; Catherine R. Gutman, all of Durham, N.C.

[73] Assignee: Duke University, Durham, N.C.

[21] Appl. No.: 539,328

[22] Filed: Oct. 4, 1995

[51] Int. Cl.$^6$ .............. C07K 1/22; C07K 14/47; C07K 14/775
[52] U.S. Cl. .............. 530/359; 530/412; 530/417
[58] Field of Search .............. 530/359, 415, 530/412, 350, 417; 436/71, 825

[56] References Cited

U.S. PATENT DOCUMENTS 5,436,169  7/1995  Iovanna et al. .............. 436/518

OTHER PUBLICATIONS

A. Kagan et al.; Kinetics of Peritoneal Protein Loss During CAPD: II. Lipoprotein Leakage and its Impact on Lasma Lipid Levels, *Kidney International* 37:980–990 (1990).

Driscoll et al., "Extrahepatic Synthesis of Apolipoprotein E", *Journal of Lipid Research*, vol. 25, 1984, pp. 1368–1379.

Garber et al., "Ascites Fluid Lipoproteins in Experimental Nephrotic Syndrome", *Biochimica et Biophysica Acta*, 959 (1988), pp. 253–261.

Glassock et al., "The Major Glomerulopathies", *Harrison's Principles of Internal Medicine*, 13th ed., pp. 1295–1306 (1994).

M.J. LaDu et al.; Purification of Apolipoprotein E Attenuates Isoform–specific Binding to β–Amyloid, *J. of Biological Chem.* 270. No. 16:9039–9042 (1995).

S.J. Murdoch et al.; Development of a Density Gradient Ultracentrifugation Technique for the Resolution of Plasma Lipoproteins which Avoids Apo E Dissociation, *Analytical Biochem.* 222:427–434 (1994).

S.C. Williams et al.; Dye–ligant affinity purification of human complement factor B and $\beta_2$ glycoprotein I, *J. of Immunological Methods* 157:25–30 (1993).

H.M. Wilson et al.; The isolation and characterization of high–density–lipoprotein subfractions containing apolipoprotein E from human plasma, *Biochem. J.* 284:477–481 (1992).

S. Meunier et al.; Preparative electrophoresis of human apolipoprotein E: an improved method, *J. of Lipid Research* 27:1324–1327 (1986).

S.C. Rall, Jr. et al.; Isolation and Characterization of Apolipoprotein E, *Methods in Enzymology* 128:273–287 (1986).

D. Reichl et al.; Human lymphedema fluid lipoproteins: particle size, cholesterol and apoliprotein distributions, and electron microscopic structure *J. of Lipid Research* 26:1399–1411 (1985).

Affi–Gel® Blue Affinity Chromatography Gel for Enzyme and Blood Protein Purifications, *EG Bulletin 1107*, BioRad Laboratories, Hercules, CA, USA (1994).

J.J. Winzerling et al. Lipoprotein Metabolism in Human Peritoneal Cells. Life Sciences. 1996, vol. 58, No. 19, pp. 1631–1641.

J. Bass et al. Macrophages from Nephrotic Rats. J. Clin. Invest. Feb. 1991, vol. 87, pp. 470–475.

*Primary Examiner*—Jeffrey E. Russel
*Attorney, Agent, or Firm*—Bell, Seltzer, Park & Gibson

[57] ABSTRACT

Peritoneal fluid and peritoneal wash fluid provide a source of abundant apolipoprotein E. Methods for isolating apolipoprotein E from peritoneal fluid or peritoneal wash fluid are provided.

9 Claims, No Drawings

SOURCE OF APOLIPOPROTEIN E AND METHOD OF ISOLATING APOLIPOPROTEIN E

FIELD OF THE INVENTION

The present invention relates to a method of isolating the lipid transport protein apolipoprotein E from peritoneal fluid.

BACKGROUND OF THE INVENTION

Apolipoprotein E (Apo E) is a lipid transport protein that exists in humans in three common isoforms: apolipoprotein E2, apolipoprotein E3, and apolipoprotein E4 (abbreviated ApoE2, ApoE3, and ApoE4, respectively). These isoforms exist at a frequency of about 8%, 76% and 16% respectively, in the population of the United States. (See, e.g., J. Poirier et al., Lancet 342, 697 (1993)). In blood, the majority of apolipoprotein E is bound to phospholipids containing cholesterol.

ApoE4 is genetically associated with late-onset familial and sporadic Alzheimer's disease. See, e.g., W. Strittmatter et al., Proc. Natl. Acad. Sci. U.S.A. 90, 1977 (1993)). The possession of an Apo E4 allele has been shown to be a risk factor for the development of Alzheimer's Disease while possession of an allele of the isoform Apo E2 has been shown to have a protective or delaying effect on the onset of this disease. (See PCT Application No. 5405-75B-1 of Roses et al.). The allele frequency of ApoE4 is highly statistically increased in patients in late-onset Alzheimer's disease families. By age 80 years, virtually all individuals who are homozygous for Apo E4 will develop Alzheimer's disease. See E. Corder et al., Science 261, 921 (1993), Apo E2 is genetically associated with cardiovascular disease. See, e.g., R. Mahley, Science 240, 622 (1988). In mice, the absence of a functional Apo E gene is associated with hypercholesterolemia. (See J. Piedrahita et al., Proc. Natl. Acad. Sci. 89, 4471 (1992)).

Recombinant Apo E is commercially available and is used, for example, in studies of Alzheimer's disease. Methods of diagnosing Alzheimer's disease (or a predisposition for Alzheimer's disease) based on the Apo E allelic state of an individual are known (see U.S. patent application Ser. No. 08/227,044 (Roses et al.), filed Apr. 13, 1994 and allowed Jul. 27, 1995, now U.S. Pat. No. 5,508,167; and U.S. patent application Ser. No. 08/441,001 (Roses et al.), filed May 15, 1995; the contents of all U.S. patents referenced herein are intended to be incorporated herein in their entirety). Purified isoforms of Apo E are useful as experimental controls in such diagnostic methods, or as quality controls in the development and manufacture of such diagnostic methods.

In view of the foregoing, there is a need for inexpensive and convenient methods of obtaining Apolipoprotein E, and for methods of obtaining Apo E of known isoforms, and for methods of purifying Apolipoprotein E.

SUMMARY OF THE INVENTION

An object of the present invention is to provide a method of isolating apolipoprotein E by providing a sample of peritoneal fluid or peritoneal wash fluid, and then isolating apolipoprotein E from the sample.

It is a further object of the present invention to provide a method of isolating apolipoprotein E from peritoneal fluid or peritoneal wash fluid, where the fluid is contacted to Cibacron Blue F3GA dye under conditions so that apolipoprotein E binds to the dye, and then eluting bound apolipoprotein E from the dye.

A further object of the present invention is to provide a method of isolating apolipoprotein E from a sample of peritoneal fluid or peritoneal wash fluid, where fatty acids are added to the sample to minimize binding of albumin to Cibacron Blue F3GA dye, and the sample is then contacted with Cibacron Blue F3GA dye under conditions which allow binding of apolipoprotein E to the dye, and then eluting apolipoprotein E which is bound to the dye.

The foregoing and other objects and aspects of the present invention are explained in detail in the specification set forth below.

DETAILED DESCRIPTION OF THE INVENTION

Methods for isolating native Apo E from blood are known (Rall SC et al., Methods in Enzymology 128:273 (1986)). However, only about 40 µg of Apo E is found per milliliter of normal human sera (less than 0.1% of the total protein). Hypertriglyceridemic subjects may have larger proportions of Apo E in blood (Rall SC et al., Methods in Enzymology 128:273 (1986)). Smaller proportions of Apo E (less than half of plasma concentrations) have also been reported as present in lymphedema fluid from patients with chronic primary lymphedema. Reichl D et al., J. Lipid Research 26:1399 (1985).

Fifty liters of normal human blood may be required to obtain 100 milligrams of Apo E; blood from multiple subjects (over 100 human donors) must be pooled to provide 50 liters of blood. Such large quantities of blood are expensive to obtain, and any pooling of samples increases the possibility of vital contamination. Further, sera is not practical as a large scale source of isoform specific Apo E, as it is not practical to isotype large numbers of donor subjects to identify those who are homozygous for an isoform.

The majority of Apo E from sera is associated with lipoprotein particles. Purification of Apo E from sera requires de-lipidation with organic solvents or detergents, which causes significant protein denaturation. Lipoprotein isolation by ultracentrifugation, with subsequent lyophilization and delipidation of lipoproteins, and chromatographic isolation of apolipoprotein E, is described in Rall et al. (1986). An alternative method for isolation of Apo E from a mixture of apolipoproteins utilizes gel electrophoresis. Purification of Apo E isoforms may be accomplished using isoelectric focusing techniques (Rall et al., (1986)).

Apo E may also be separated from contaminating proteins using heparin-sepharose chromatography, which utilizes the heparin-binding property of Apo E (Rall et al., (1986)). Separation of the non-cysteine containing E-4 isoform of Apo E from contaminating cysteine-containing proteins may be accomplished using thiopropyl chromatography on thiopropyl Sepharose (Weisgraber KH et al., J. Biol. Chem. 258:2508 (1983)).

Recombinant Apo E can be produced using methods known in the art, and human recombinant Apo E is commercially available. However, recombinant protein is not in the native glycosylated form and is subject to denaturation and oxidation during purification.

The present inventors have discovered that peritoneal wash fluid, which in humans is produced as a byproduct of medically indicated peritoneal dialysis, contains a significant amount of Apo E. Samples of human peritoneal wash fluid in which Apo E constituted about 1% of the total protein have been identified. Peritoneal wash fluid produced during peritoneal dialysis of human subjects is currently considered waste.

Peritoneal dialysis is used in treating subjects with renal failure, and is in many cases an alternative to hemodialysis. A surgically placed peritoneal catheter provides access to the peritoneal cavity and the process is carried out using an automated dialysis device. Physiologic fluid (dialysate) is introduced into the peritoneal cavity through the catheter, and is left in place for a time to allow solute to diffuse from the blood across the peritoneal membrane into the dialysate, which is then removed.

It is readily apparent that, as the physiologic fluid used in peritoneal dialysis does not contain Apo E, the Apo E present in peritoneal wash fluid is a component of peritoneal fluid. As used herein, peritoneal fluid refers to fluids naturally present in the peritoneum. As used herein, peritoneal wash fluid refers to a mixture of peritoneal fluid and physiologic fluid which has been introduced into the peritoneum. Methods described herein as useful in treating peritoneal wash fluid are similarly useful in treating peritoneal fluid obtained by means other than peritoneal dialysis.

Because large quantities of peritoneal wash fluid can be obtained from a single subject (up to 10 liters per human peritoneal dialysis patient per day), it is possible to obtain large quantities of Apo E from a single subject. It is thus feasible to isotype subjects to identify those subjects homozygous for an Apo E isoform, to obtain quantities of a single isoform of Apo E.

The Apo E allelic state of an individual can be determined, and subjects homozygous for Apo E2, Apo E3 or Apo E4 can be identified; the allelic state of Apo E obtained from these subjects will thus be known. Assays capable of distinguishing between Apo E2, Apo E3, and Apo E4 include immunoassays, isoelectric focusings, and PCR analysis of DNA encoding Apo E2, Apo E3, and Apo E4. Those skilled in the art will be familiar with numerous specific immunoassay formats and variations thereof which may be useful for identifying the allelic state of a subject. See generally E. Maggio, *Enzyme-Immunoassay*, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al., U.S. Pat. No. 4,376,110 to David et al., U.S. Pat. No. 4,275,149 to Litman et al., U.S. Pat. No. 4,233,402 to Maggio et al., and U.S. Pat. No. 4,230,767 to Boguslaski et al. See also U.S. patent application Ser. No. 08/227,044 (Roses et al.), filed Apr. 13, 1994 and allowed Jul. 27, 1995, now U.S. Pat. No. 5,508,167.

Apo E isolated from peritoneal wash fluid is less likely to be contaminated with virus, as there is no need to pool samples from multiple subjects. Subjects may also be monitored for vital infections; human patients receiving therapeutic peritoneal dialysis typically are routinely monitored for viral infections.

The present method of isolating apolipoprotein E involves obtaining peritoneal fluid or peritoneal wash fluid from a subject and isolating the Apo E therein. Any suitable method of isolating Apo E may be used with the peritoneal wash fluid, including but not limited to methods utilizing ultracentrifugation with subsequent lyophilization and chromatographic isolation of apolipoprotein E, gel electrophoresis, heparin-sepharose chromatography, or thiopropyl chromatography, as are known in the art.

The present inventors have also developed a protocol for isolating Apo E, based on their finding that Apo E from peritoneal fluid binds selectively to the dye Cibacron Blue F3GA (also known as Cibacron Blue 3G-A, Reactive Blue 2, and Procion Blue H-B). Cibacron Blue F3GA is a triazine dye used in dye-ligand chromatography for the purification of proteins, and is available commercially in an agarose gel preparation AFFI-GEL® Blue Affinity Chromatography Gel (agarose gel preparation containing Cibacron Blue F3GA dye), Bio-Rad Laboratories, Hercules, Calif., U.S.A.; 1-800-4BIORAD (United States and Canada)). AFFI-GEL® Blue (agarose gel preparation containing Cibacron Blue F3GA dye) is a beaded, cross-linked agarose gel with covalently attached Cibacron Blue F3GA dye. See EG Bulletin 1107, Bio-Rad Laboratories, for a discussion of the AFFI-GEL® (agarose gel preparation containing Cibacron Blue F3GA dye) product. The dye acts as an ionic, hydrophobic, aromatic or sterically active binding site. The present method of purification uses agarose coupled to Cibacron Blue F3GA for affinity purification of Apo E from biological fluids containing Apo E.

While not wishing to be limited to a single theory, the present data indicate that Apo E contained in peritoneal wash fluid binds to Cibacron Blue F3GA through hydrophobic interactions. Similar interactions are involved in the binding of Apo E to lipids.

The present inventors further found that Apo E in peritoneal fluid bound to heparin-agarose, although to a lesser degree than to Cibacron Blue F3GA-agarose. The heparin binding property of Apo E has previously been utilized for isolating Apo E by heparin-sepharose chromatography. Rall et al., *Methods in Enzymology*, 128:273 (1986).

As used herein, isolation of Apo E refers to the separation of apolipoprotein E from other proteins present in biologic fluid such as blood or peritoneal fluid. Isolation may occur in a multi-step process, each step producing products containing increased concentrations of Apo E. Isoforms of Apo E may be isolated from a sample of apoE using methods known in the art. As used herein, isolation or purification of apoE means methods which eliminate non-apoE components from a starting material to produce a product with an enriched Apo E component.

One present method of isolating Apo E from peritoneal fluid utilizes the ability of apolipoprotein E in peritoneal fluid to bind to Cibacron Blue F3GA. The method comprises contacting the fluid to Cibacron Blue F3GA under conditions that allow apolipoprotein E to bind to the dye, removing unbound materials, and recovering the bound apolipoprotein E from the dye. The dye may be bound to a substrate such as agarose. The peritoneal fluid may be treated to minimize binding of albumin (naturally present in peritoneal fluid) to the dye. A fatty acid or equivalent compound, for example, may be added to the fluid prior to contact with the dye to reduce, minimize or prevent albumin binding to Cibacron Blue F3GA.

A particular embodiment of the present method comprises obtaining peritoneal wash fluid from human subjects; adding, combining or mixing a fatty acid with the peritoneal wash fluid; contacting the peritoneal wash fluid with Cibacron Blue F3GA dye under conditions which allow apolipoprotein E to bind to the dye; removing unbound material (for example, by washing under conditions which allow the apolipoprotein to remain bound to the dye); and recovering bound apolipoprotein E from the dye (for example, by eluting and precipitating the Apo E). The present inventors have determined various conditions under which Apo E from peritoneal fluid will bind to, will remain bound, will be prevented from binding, or will be eluted from Cibacron Blue F3GA (see Table 2). Apo E bound to the Cibacron Blue F3GA may be eluted using Cibacron Blue F3GA (e.g., 20 mg/ml Cibacron Blue F3GA) or by using deoxycholate (e.g., 0.2% deoxycholate). The present inventors have also found that Apo E isolated from peritoneal fluid is soluble in about 40% ammonium sulfate and will precipitate in higher concentrations of ammonium sulfate. The protein precipitate obtained from ammonium sulfate fractionation may then be further purified using methods known in the art. See, e.g., Rall SC et al., *Methods in Enzymology* 128:273 (1986); Weisgraber KH et al., *J. Biol. Chem.* 258:2508 (1983).

In light of the present inventors' discovery that peritoneal fluid is a source of abundant apolipoprotein E, additional methods suitable for isolating apolipoprotein E from peritoneal fluid will be apparent to those in the art. As shown herein, apolipoprotein E in peritoneal fluid was found to bind to heparin-agarose (Table 1). Apo E from peritoneal fluid was further found to bind to Cibacron Blue F3GA; dyes with binding characteristics equivalent to Cibacron Blue F3GA can also be utilized in the present methods.

Subjects suitable for carrying out the present invention are, in general, mammals, including but not limited to humans, monkeys, equines, captines, bovines, ovines, porcines, dogs, cats, rabbits, rats, and mice. Human subjects are presently preferred. Subjects may be homozygous or heterozygous for Apo E isoforms. In humans, Apo E isoforms have been identified as Apo E2, Apo E3 and Apo E4; human subjects may be homozygous or heterozygous for these Apo E isoforms.

Apo E collected by the present invention may be further isolated and/or purified, optionally to homogeneity, by conventional techniques such as affinity chromatography, size-exclusion chromatography, gas chromatography, HPLC, and combinations thereof.

Apo E produced by the method of the invention is useful as an immunogen in the manufacture of antibodies, which antibodies are useful in immunoassays for screening for cardiovascular disease and Alzheimer's disease.

The following examples are provided to illustrate the present invention, and should not be construed as limiting thereof. In these examples, M means molar, mM means millimolar, ml means milliliter, mg means milligram, rpm means revolutions per minute, DTT means dithiothreitol, and TBS means tris buffered saline.

EXAMPLE 1

Peritoneal Wash Fluid Contains Abundant Apo E

Samples of human peritoneal wash fluid from human subjects undergoing medically indicated peritoneal dialysis were obtained from ten different individuals. Fluid was maintained at room temperature (i.e., was not chilled), and was transported to the laboratory and processed soon after collection.

Peritoneal wash fluid samples were analyzed by standard Western blot procedures using anti-human Apo E antibody (available from Cal Biochem). Each sample was found to contain between 1–10 μg Apo E/ml of peritoneal wash fluid, which represented approximately 0.1–1% of the total protein. Protein was assessed using the BioRad Bradford assay (BioRad Laboratories, Hercules, Calif.).

Using 60% ammonium sulfate, more than 95% of the Apo E present in peritoneal wash fluid is precipitated, suggesting that the Apo E was not associated with lipids as is Apo E isolated from blood.

The above results indicate that peritoneal wash fluid is a source of abundant Apo E.

EXAMPLE 2

Collection of Peritoneal Fluid for Isolation of Apo E

Peritoneal wash fluid samples were obtained from human subjects undergoing medically indicated peritoneal dialysis. Samples were processed as soon as feasible after collection to minimize absorption of Apo E by plastic dialysis bags or trapping of Apo E in fibrin clots which develop over time. Samples were not chilled to minimize any loss of available Apo E caused by increased fibrin precipitation due to chilling.

EXAMPLE 3

Investigation of Apo E Binding Characteristics

The binding of Apo E from peritoneal wash fluid to various agarose affinity matrices was investigated. Each of the seven different matrices listed in Table 1 was incubated with a fixed amount of peritoneal wash fluid. The matrix was washed to remove unbound material and then boiled in sample buffer and analyzed by Western Blot methods, using standard anti-Apo E antibodies (Cal-Biochem). The extent of binding was assessed subjectively by reviewing Western blot results; (−) indicates no binding; (+) indicates weak binding; (++) or (+++) indicates moderate binding; and (++++) or (+++++) indicate extensive binding.

As shown in Table 1, Apo E from peritoneal wash fluid did not bind to Agarose or to CM-Agarose; bound poorly to DEAE-Agarose; and bound moderately to heparin agarose and Cibacron Blue F3GA-agarose (AFFI-GEL® Blue (agarose gel preparation containing Cibacron Blue F3GA dye)) with carboxymethyl. Apo E from peritoneal wash fluid bound extensively to Cibacron Blue F3GA-agarose (AFFI-GEL® Blue (agarose gel preparation containing Cibacron Blue F3GA dye)), and bound most strongly to Cibacron Blue F3GA-agarose (AFFI-GEL® (agarose gel preparation containing Cibacron Blue F3GA dye)) with diethylaminoethyl. However, Apo E bound to DEAE AFFI-GEL® (agarose gel preparation containing Cibacron Blue F3GA dye) was difficult to recover. Elution from this matrix required a combination of high salt with either deoxycholate or Cibacron Blue F3GA dye. Such elution conditions are more denaturing than conditions suitable for Apo E bound to Cibacron Blue F3GA-agarose.

The above data indicate that Apo E contained in peritoneal fluid binds strongly to Cibacron Blue F3GA. Apo E from peritoneal fluid binds efficiently to Cibacron Blue F3GA-agarose (AFFIG-GEL® (agarose gel preparation containing Cibacron Blue F3GA dye)), where it can be washed with a variety of agents and eluted simply.

TABLE 1

Agarose Affinity Matrices: Binding of Apo E from Peritoneal Wash Fluid

| Affinity Matrix | Reactive Groups | Binding to Apo E[1] |
|---|---|---|
| DEAE-Agarose | diethylaminoethyl | + |
| CM-Agarose | carboxymethyl | − |
| Agarose | none, free support | − |
| Cibacron Blue F3GA-Agarose[3] | Cibacron Blue F3GA | ++++ |
| CM AFFI-GEL® Blue[2] | carboxymethyl and Cibacron Blue F3GA | +++ |
| DEAE AFFI-GEL® Blue[3] | diethylaminoethyl and Cibacron Blue F3GA | +++++[2] |
| Heparin Agarose | heparin | ++ |

[1]Binding was assessed subjectively; (−) indicates no binding; (+) indicates weak binding; (++) or (+++) indicates moderate binding, and (++++) or (+++++) indicate extensive binding.
[2]DEAE AFFI-GEL® Blue bound Apo E, however, it was difficult to recover the protein from the matrix.
[3]AFFI-GEL® Blue (Bio-Rad Laboratory, Hercules CA).

EXAMPLE 4

Binding and Elution Properties of Apo E

The binding and elution properties of Apo E to an agarose gel with covalently attached Cibacron Blue F3GA dye (AFFI-GEL® Blue (agarose gel preparation containing Cibacron Blue F3GA dye), Bio-Rad Laboratories, Hercules Calif.) were determined to be as follows (see also Table 2).

Apo E was found to bind to an a garose gel with covalently attached Cibacron Blue F3GA dye (Affi-Gel® Blue Bio-Rad Laboratories, Hercules Calif.) in 1M salt; 1M salt with 25 mM caprylate; 25 mM caprylate; 25% ethylene glycol; or 1M salt with 1.5M urea.

Apo E did not bind to an agarose gel with covalently attached Cibacron Blue F3GA dye (AFFI-GEL® Blue (agarose gel preparation containing Cibacron Blue F3GA dye), Bio-Rad Laboratories, Hercules Calif.) in 5 mg/ml Cibacron Blue F3GA or 1% deoxycholate.

Apo E which is bound to an agarose gel with covalently attached Cibacron Blue F3GA dye (AFFI-GEL® Blue (agarose gel preparation containing Cibacron Blue F3GA dye), Bio-Rad Laboratories, Hercules Calif.) remains bound in: 1M salt; 1.5M urea; 1M salt; 25% ethylene glycol; 50% ethylene glycol and 150 mM salt; 100 mM DTT, TBS; 1% NP40, TBS; or 150 mM salt with 0.5 mg/ml Cibacron Blue F3GA.

Apo E bound to an agarose gel with covalently attached Cibacron Blue F3GA dye (AFFI-GEL® Blue (agarose gel preparation containing Cibacron Blue F3GA dye), Bio-Rad Laboratories, Hercules Calif.) elutes in: 20 mg/ml Cibacron Blue F3GA in 500 mM salt or 0.2% deoxycholate.

Cibacron Blue F3GA dye acts, in varied applications, as an ionic, hydrophobic, aromatic or sterically active binding site. Proteins are normally eluted from a gel with Cibacron Blue F3GA dye (AFFI-GEL® Blue (agarose gel preparation containing Cibacron Blue F3GA dye), Bio-Rad Laboratories, Hercules, Calif.) by either disrupting ionic interactions with salt, by denaturing the protein with urea, or by interfering with hydrophobic interactions using detergents. As shown by the method of purifying Apo E of Example 5, below, Apo E apparently binds to Cibacron Blue F3GA dye through a highly

TABLE 2

Apo E Binding to Cibacron Blue F3GA Dye

|  | Apo E Binds | Apo E remains bound | Apo E does not bind | Apo E elutes |
|---|---|---|---|---|
| 1M salt | X | X | | |
| 1M salt, 25 mM caprylate | X | | | |
| 25 mM caprylate | X | | | |
| 25% ethylene glycol | X | X | | |
| 1M salt, 1.5M urea | X | X | | |
| 50% ethylene glycol 150 mM salt | | X | | |
| 100 mM DTT, TBS | | X | | |
| 1% NP40, TBS | | X | | |
| 150 mM salt, 0.5 mg/ml Cibacron* | | X | | |
| 5 mg/ml Cibacron* | | | X | |
| 1% dexoycholate | | | X | |
| 20 mg/ml Cibacron*, 500 mM salt | | | | X |
| 0.2% deoxycholate | | | | X |

*Cibacron = Cibacron Blue F3GA selective mechanism. High concentrations of salt and urea did not disrupt Apo E binding to AFFI-GEL® Blue (agarose gel preparation containing Cibacron Blue F3GA dye), suggesting the interaction of Apo E and Cibacron Blue F3GA is hydrophobic in nature. This interaction is selective, as shown by the fact that non-ionic detergents vary in effect on Apo E binding to Cibacron Blue F3GA.

EXAMPLE 5

Isolation of Apo E Using Cibacron Blue F3GA Dye

As noted in Example 3, the present inventors found that Apo E present in peritoneal wash fluid bound to Cibacron Blue F3GA dye. The following method was developed to use this factor to isolate Apo E from peritoneal fluid.

A two liter sample of peritoneal wash fluid was obtained as described in Example 2. The primary contaminating protein in peritoneal fluid is albumin, which also binds to Cibacron Blue F3GA; this binding is inhibited by the presence of fatty acids (Williams SC and Sim RB, *J. Immunological Methods* 157:25 (1993)). The peritoneal wash fluid was therefore adjusted to 50 mM caprylate for 15 minutes and then adjusted to 1M salt, to minimize subsequent albumin binding to the gel matrix. Twenty mls of AFFI-GEL® Blue (agarose gel preparation containing Cibacron Blue F3GA dye) (Bio-Rad Laboratory, Hercules Calif.) beads were added to the fluid for 30 minutes with occasional mixing. The fluid and beads were then packed into a column and sequentially washed with 20 mls of each of the following solutions: 1M salt; 150 mM salt; 150 mM salt with 25% ethylene glycol; 150 mM salt; 150 mM salt with 0.5 mg/ml Cibacron Blue F3GA; 150 mM salt; 100 mM DTT, TBS; 150 mM salt; 0.5% NP40, TBS; 150 mM salt; and 500 mM salt. Apo E was found to bind to, or remain bound to, Cibacron Blue F3GA dye in these solutions (Table 2).

Apo E was eluted with 20 mg/ml Cibacron Blue F3GA. In an alternative protocol, Apo E was eluted with 0.2% deoxycholate.

Apo E was then fractionated by ammonium sulfate precipitation. Apo E was found to be soluble in 40% ammonium sulfate and to precipitate in greater concentrations of ammonium sulfate. Ammonium sulfate concentration of about 60%, or about 60% and greater, were suitable for precipitating Apo E. (See Example 1).

EXAMPLE 6

Further Purification of Apo E from Peritoneal Fluid

The protein precipitate obtained from ammonium sulfate fractionation (Example 5) is then further purified by methods known in the art. See, e.g., Rall SC et al., *Methods in Enzymology* 128:273 (1986); Weisgraber KH et al., *J. Biol. Chem.* 258:2508 (1983).

The Apo E obtained in Example 5 is first extracted in chloroform/methanol to remove any remaining lipids and detergents from the protein. The ammonium sulfate pellet is solubilized in 15 mls of ice cold chloroform/methanol (2:1) and placed on ice for 1 hour; after 1 hour on ice, 10 mls (2 parts) methanol is added and the solution is centrifuged at 2000 rpm for 5 minutes. The pellet is resuspended in 15 mls of chloroform/methanol (2:1) and then 10 mls of methanol is added and the mixture again centrifuged. The resulting pellet is washed in ice cold methanol, resuspended and fractionated by gel filtration. Rall et al., *Methods in Enzymology* 128:273 (1986).

The above protocol provides a method of purifying Apo E protein isolated from peritoneal wash fluid using Cibacron Blue F3GA dye.

The foregoing is illustrative of the present invention and is not to be construed as limiting thereof. The invention is defined by the following claims, with equivalents of the claims to be included therein.

That which is claimed is:

1. A method of isolating apolipoprotein E, comprising:
   (a) providing a sample of human peritoneal fluid or human peritoneal wash fluid;
   (b) isolating apolipoprotein E from said sample.

2. A method according to claim 1 wherein said sample is obtained from a subject whose apolipoprotein E allelic state is known.

3. A method according to claim 1 wherein said isolating step comprises:
   (a) contacting said sample to cibacron Blue F3GA dye under conditions that permit binding of apolipoprotein E to said dye; and
   (b) eluting bound apolipoprotein E from said dye.

4. A method according to claim 3 where, prior to said contacting step, fatty acids are added to said sample in an amount effective to minimize binding of albumin to Cibacron Blue F3GA dye.

5. A method of isolating apolipoprotein E from human peritoneal fluid or human peritoneal wash fluid, comprising the steps of contacting said fluid to Cibacron Blue F3GA dye under conditions so that apolipoprotein E binds to said dye, and then eluting bound apolipoprotein E from said dye.

6. A method according to claim 5 where, prior to contacting said fluid to said dye, fatty acids are added to said fluid in an amount effective to minimize binding of albumin to Cibacron Blue F3GA dye.

7. A method according to claim 5 wherein said sample is obtained from a subject whose apolipoprotein E allelic state is known.

8. A method of isolating apolipoprotein E from a sample of human peritoneal fluid or human peritoneal wash fluid comprising the steps of:
   (a) adding fatty acids to a sample of human peritoneal fluid or human peritoneal wash fluid in an amount effective to minimize binding of albumin to Cibacron Blue F3GA dye;
   (b) contacting said sample from step (a) with Cibacron Blue F3GA dye under conditions which allow binding of apolipoprotein E to said dye; and
   (c) eluting apolipoprotein E bound to said dye.

9. A method according to claim 8 wherein said sample is obtained from a subject whose apolipoprotein E allelic state is known.

* * * * *